(12) United States Patent
Kodis

(10) Patent No.: US 7,568,644 B1
(45) Date of Patent: Aug. 4, 2009

(54) CUTTING SYSTEM

(75) Inventor: Robert D. Kodis, Chestnut Hill, MA (US)

(73) Assignee: Infection Management, Inc., Andover, MA (US)

( * ) Notice: Subject to any disclaimer, the term of this patent is extended or adjusted under 35 U.S.C. 154(b) by 0 days.

(21) Appl. No.: 12/121,124

(22) Filed: May 15, 2008

Related U.S. Application Data

(62) Division of application No. 12/120,643, filed on May 14, 2008.

(51) Int. Cl.
*B02C 18/08* (2006.01)

(52) U.S. Cl. ............... 241/158; 241/160; 241/236

(58) Field of Classification Search ............ 241/236, 241/160, 158, 36, 60
See application file for complete search history.

(56) References Cited

U.S. PATENT DOCUMENTS

| | | | |
|---|---|---|---|
| D282,009 S | 12/1985 | Gianni |
| D282,286 S | 1/1986 | Gianni |
| 4,886,164 A | 12/1989 | Stein et al. |
| 4,911,294 A | 3/1990 | Russo et al. |
| 4,971,261 A | 11/1990 | Solomons |
| 4,979,683 A | 12/1990 | Busdeker |
| 5,005,496 A | 4/1991 | Nagata et al. |
| 5,025,994 A | 6/1991 | Maitlen et al. |
| 5,035,367 A | 7/1991 | Nojima et al. |
| 5,054,696 A | 10/1991 | Mennel et al. |
| 5,064,124 A | 11/1991 | Chang et al. |
| 5,078,508 A | 1/1992 | Johan et al. |
| 5,080,251 A | 1/1992 | Noack |
| 5,096,128 A | 3/1992 | Chang et al. |
| 5,097,950 A | 3/1992 | Weiss et al. |
| 5,106,594 A | 4/1992 | Held et al. |
| 5,119,994 A | 6/1992 | Placzek |
| 5,148,940 A | 9/1992 | Mendise |
| 5,173,257 A | 12/1992 | Pearson |
| 5,178,828 A | 1/1993 | Uesugi et al. |
| 5,186,397 A | 2/1993 | Orlando |
| 5,193,468 A | 3/1993 | McRae |
| D334,805 S | 4/1993 | Ivey |
| 5,209,411 A | 5/1993 | Dineley et al. |
| 5,217,688 A | 6/1993 | Von Lersner |
| 5,223,231 A | 6/1993 | Drake |
| 5,236,135 A | 8/1993 | Wilson et al. |
| 5,240,187 A | 8/1993 | Wilson |
| 5,242,434 A | 9/1993 | Terry |
| 5,248,486 A | 9/1993 | Matsuoka et al. |
| 5,252,290 A | 10/1993 | Uesugi et al. |
| 5,256,861 A | 10/1993 | Anthony |
| 5,269,454 A | 12/1993 | Perazzo |
| 5,269,457 A | 12/1993 | de la Fuente |
| 5,271,341 A | 12/1993 | Wagner |
| 5,277,136 A | 1/1994 | Davis |
| 5,291,746 A | 3/1994 | Abbott |
| 5,294,412 A | 3/1994 | Orlando |
| 5,304,711 A | 4/1994 | Tanaka et al. |

(Continued)

*Primary Examiner*—Faye Francis
(74) *Attorney, Agent, or Firm*—Scott E. Kamholz; Foley Hoag LLP

(57) ABSTRACT

A cutting system may include a first-stage cutting system having a fixed cutter against which rotate two interleaving sets of rotary cutters, and a second-stage cutting system having a fixed cutter against which rotates a rotary cutter. A chute may channel material emerging from the first-stage cutting system into the second-stage cutting system.

20 Claims, 11 Drawing Sheets

U.S. PATENT DOCUMENTS

| | | | |
|---|---|---|---|
| 5,339,959 A | 8/1994 | Cornwell | |
| 5,340,039 A | 8/1994 | Lefevre | |
| 5,346,142 A | 9/1994 | Miller et al. | |
| 5,346,235 A | 9/1994 | Holman | |
| 5,348,704 A | 9/1994 | Tanaka | |
| D351,906 S | 10/1994 | Marsh | |
| 5,360,594 A | 11/1994 | Meijer | |
| 5,362,443 A | 11/1994 | Tanaka et al. | |
| 5,364,589 A | 11/1994 | Buehler et al. | |
| 5,374,394 A | 12/1994 | Kralovic | |
| 5,397,068 A | 3/1995 | Solomons et al. | |
| 5,397,535 A | 3/1995 | Kaneko et al. | |
| 5,427,238 A | 6/1995 | Weiss | |
| 5,429,315 A | 7/1995 | Wollert et al. | |
| 5,433,412 A | 7/1995 | Watt et al. | |
| 5,447,685 A | 9/1995 | Sievert et al. | |
| 5,465,841 A | 11/1995 | Wilson et al. | |
| 5,494,186 A | 2/1996 | Marsh | |
| 5,508,004 A | 4/1996 | Held et al. | |
| 5,511,657 A | 4/1996 | Gnau, III et al. | |
| 5,516,052 A | 5/1996 | Adams et al. | |
| 5,520,888 A | 5/1996 | Berndt | |
| 5,533,681 A | 7/1996 | Riley | |
| 5,534,162 A | 7/1996 | Adams et al. | |
| 5,562,255 A * | 10/1996 | Witko et al. | 241/158 |
| 5,588,174 A | 12/1996 | Godfrey | |
| 5,590,840 A | 1/1997 | Adams et al. | |
| 5,595,711 A | 1/1997 | Wilson et al. | |
| 5,620,654 A | 4/1997 | Mosenson et al. | |
| 5,626,086 A | 5/1997 | Malone | |
| 5,639,035 A * | 6/1997 | Maugle et al. | 241/236 |
| 5,641,947 A | 6/1997 | Riddle, Jr. | |
| 5,647,502 A | 7/1997 | Marsh | |
| 5,673,861 A | 10/1997 | Miller | |
| 5,676,070 A | 10/1997 | Maganas et al. | |
| 5,692,687 A | 12/1997 | Kateley | |
| D389,964 S | 1/1998 | Lewandowski et al. | |
| 5,709,842 A | 1/1998 | Held et al. | |
| 5,799,591 A | 9/1998 | Anderson | |
| 5,830,419 A | 11/1998 | Held et al. | |
| 5,833,922 A | 11/1998 | Held et al. | |
| 5,853,450 A | 12/1998 | Burnham et al. | |
| D404,483 S | 1/1999 | Harwood et al. | |
| D411,008 S | 6/1999 | Gaba et al. | |
| 5,914,047 A | 6/1999 | Griffiths | |
| 5,917,285 A | 6/1999 | Gillis et al. | |
| D414,864 S | 10/1999 | Gaba et al. | |
| D415,273 S | 10/1999 | Gaba et al. | |
| 5,972,291 A | 10/1999 | Healy et al. | |
| D421,122 S | 2/2000 | Gaba et al. | |
| 6,027,490 A | 2/2000 | Radford et al. | |
| 6,113,854 A | 9/2000 | Milum et al. | |
| 6,126,830 A | 10/2000 | Marshall | |
| 6,186,428 B1 | 2/2001 | Robinson et al. | |
| D438,964 S | 3/2001 | Gaba et al. | |
| 6,242,664 B1 | 6/2001 | Crihan | |
| 6,262,405 B1 | 7/2001 | Wicks et al. | |
| 6,283,909 B1 | 9/2001 | Sharp et al. | |
| 6,344,638 B1 | 2/2002 | Tomasello | |
| 6,346,218 B1 | 2/2002 | Milum et al. | |
| 6,357,682 B1 | 3/2002 | Hext | |
| 6,386,386 B1 | 5/2002 | George | |
| 6,394,376 B1 * | 5/2002 | Koenig | 241/236 |
| 6,437,211 B2 | 8/2002 | Kaye et al. | |
| 6,446,887 B1 | 9/2002 | Swisher, Jr. et al. | |
| 6,450,427 B1 * | 9/2002 | Maynard | 241/160 |
| 6,472,580 B2 | 10/2002 | Kaye et al. | |
| 6,488,675 B1 | 12/2002 | Radford et al. | |
| 6,494,391 B2 | 12/2002 | Mosenson et al. | |
| 6,585,114 B2 | 7/2003 | Kennedy et al. | |
| 6,726,136 B2 | 4/2004 | Swisher, Jr. et al. | |
| 2007/0197852 A1 | 8/2007 | Wilson et al. | |

* cited by examiner

CUTTING SYSTEM

CROSS-REFERENCE TO RELATED APPLICATION

This application is a division of U.S. application Ser. No. 12/120,643, filed May 14, 2008, which is hereby incorporated herein by reference.

COMPUTER PROGRAM LISTING APPENDIX

A computer program listing is appended to this disclosure and is hereby incorporated herein by this reference. The appendix includes a single file: example-wrl.txt.

BACKGROUND

Waste processing for pathogen reduction has typically involved use of heat, cooling, pressurizing, and combinations of these to disinfect waste or place the waste in better condition for disinfection.

SUMMARY

The inventor has found that disinfection of waste can be carried out at ambient temperature and without being under pressure by first cutting the waste into small pieces to expose surfaces in the waste and then spraying the waste pieces with disinfectant. Effective disinfection is obtained thereby without having to heat, cool, or pressurize the waste during cutting or disinfection. Throughput is increased, and processing cost per unit waste is reduced, by not having to consume time or energy to heat or cool the waste.

The disclosed techniques may be employed, for example, in hospitals, where a considerable amount of the waste generated contains pathogens and so requires special handling. Systems and methods described herein may be employed to process such medical waste on-site and more quickly and cheaply compared to existing systems.

DETAILED DESCRIPTION

A waste processing method may include sealing infected waste inside a waste processing system, cutting the infected waste into pieces having cross sections no larger than one square inch, thereby exposing surfaces of the waste, and agitating the waste pieces and simultaneously spraying the waste pieces with a disinfectant that kills pathogens on contact, thereby disinfecting the waste. The method may be carried out at room temperature (i.e., without adding or removing heat from the system, aside from minimal heat generated by operation of the system's moving parts) and at or below ambient pressure (i.e., at a pressure not higher than the pressure outside the waste processing system).

Figure 1:
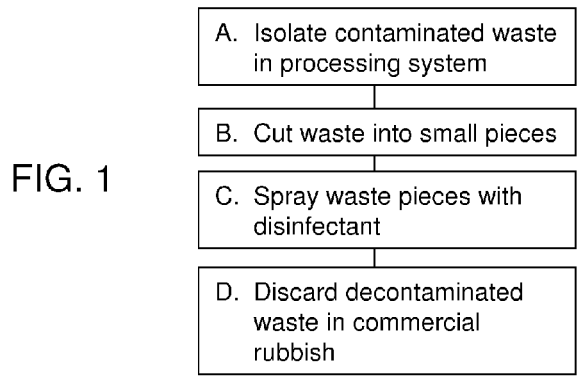
FIG. 1 depicts a flowchart of a waste processing method.

FIG. 1 depicts a flowchart of a waste processing method. Contaminated waste (also "infected waste"), i.e., pathogen-bearing waste, is (A) isolated inside the waste processing system. Isolation will typically involve airtight and liquid-tight sealing so that contaminated waste exposed during processing will not kick pathogens into the environment surrounding the system. Once the contaminated waste is sealed within the system, it is (B) subjected to a cutting process to reduce the waste to small pieces. The thickness of pieces may be substantially the thickness of the waste as it entered the system. The cutting process may typically involve shredding and shearing operations to break the waste into small pieces and to expose the surfaces of the waste to disinfectant. The cutting process would typically avoid crushing the waste unless subsequent cutting steps would serve to re-expose surfaces obscured by the crushing. The cutting process may typically also obliterate any identifying marks on the waste, such as printed characters, labels, and the like. Following the cutting process, contaminated waste pieces may resemble confetti.

The contaminated waste pieces are then (C) sprayed with disinfectant, typically liquid disinfectant in sufficient quantity to coat all or substantially all surfaces in the waste pieces. Once thus disinfected, the waste pieces may then be (D) discarded through commercial rubbish channels.

Figure 2:
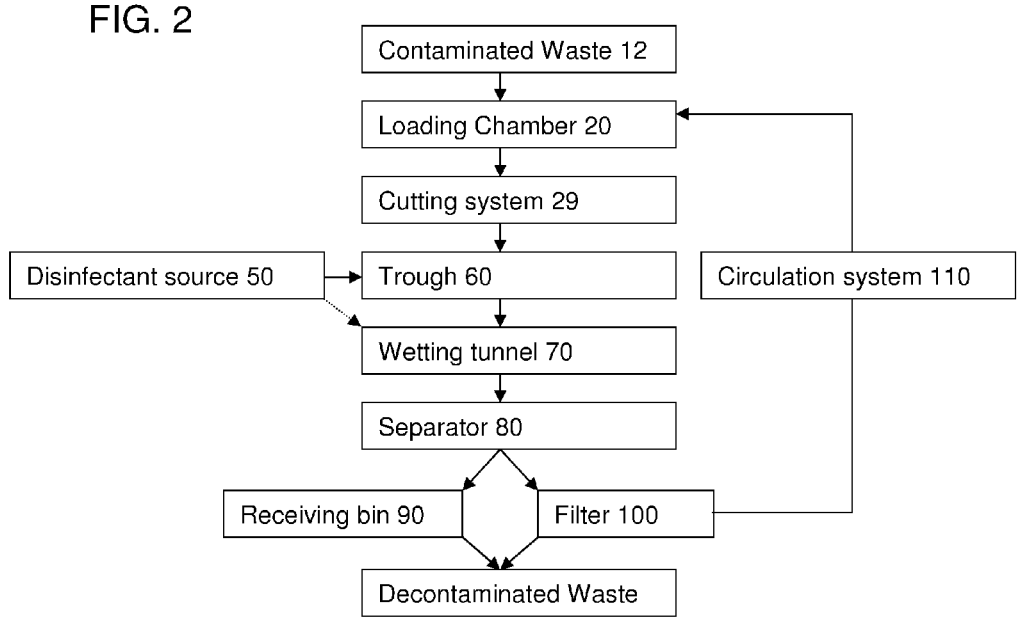
FIG. 2 depicts a schematic chart for a waste processing system.

FIG. 2 depicts a schematic chart for a waste processing system to implement the method outlined in FIG. 1. Contaminated waste 12 is introduced into the system by way of loading chamber 20 and is passed to cutting system 29 where it is cut into small pieces. Circulation system 110 applies vacuum inside the system to suck the waste from the loading chamber into the cutting system and thence through the rest of the system. If the cutting system is positioned below the loading chamber, then gravity may also help advancing the waste. Trough 60 receives the waste pieces and disinfectant from disinfectant source 50. Vacuum from the circulation system creates a wind inside the system that sweeps up the waste pieces, suspends them in the air, keeps them separate from one another, and agitates them in the trough and in subsequent sections of the system, thereby exposing as many surfaces of the waste as possible to disinfectant sprayed on the waste. All or substantially all of the surfaces may thereby be exposed to disinfectant.

The sprayed waste pieces are then sucked into wetting tunnel 70 and then deposited in separator 80, in which any particulate matter that was generated or liberated from the waste in the cutting process or agitation is separated from bulk waste pieces. Bulk waste passes into receiving bin 90, after optionally passing through a dryer (not shown), while particulate matter is directed into filter system 100, where it is trapped. Products of the waste processing system are thus bulk waste and particulate waste.

Figure 3:
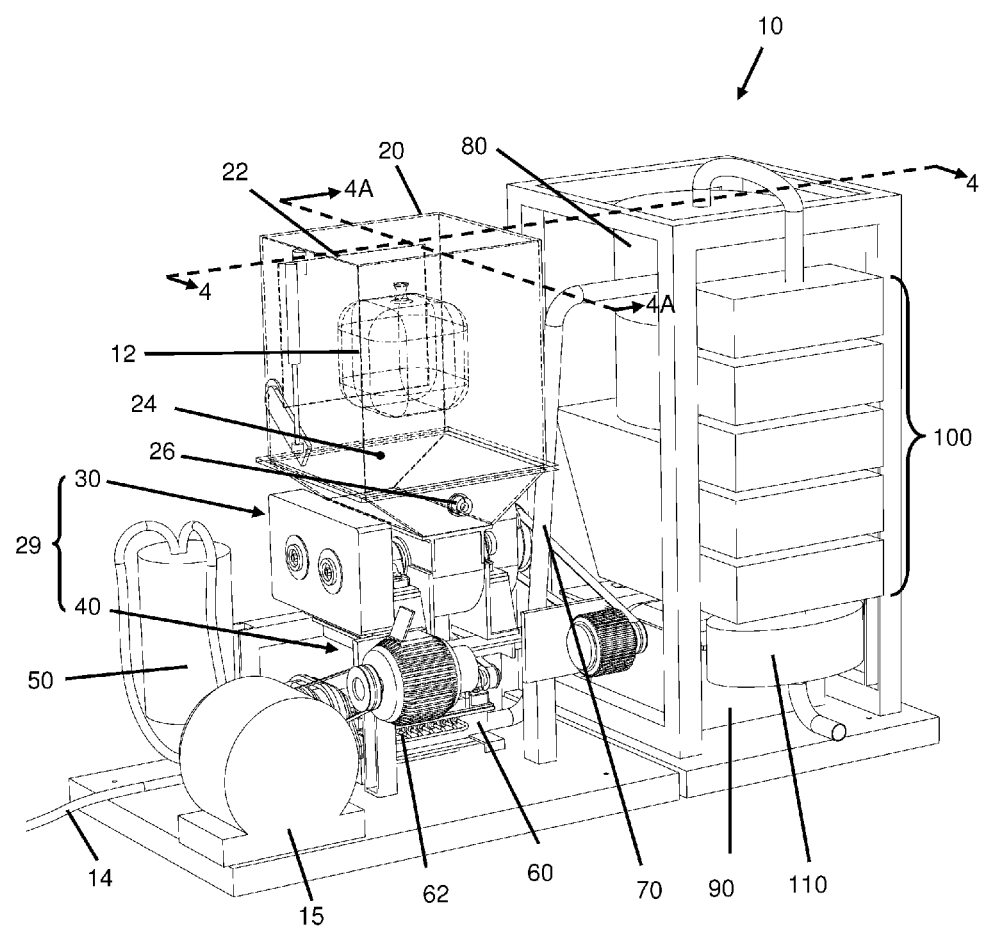
FIG. 3 illustrates an exemplary embodiment of a waste processing system.
Figure 4:
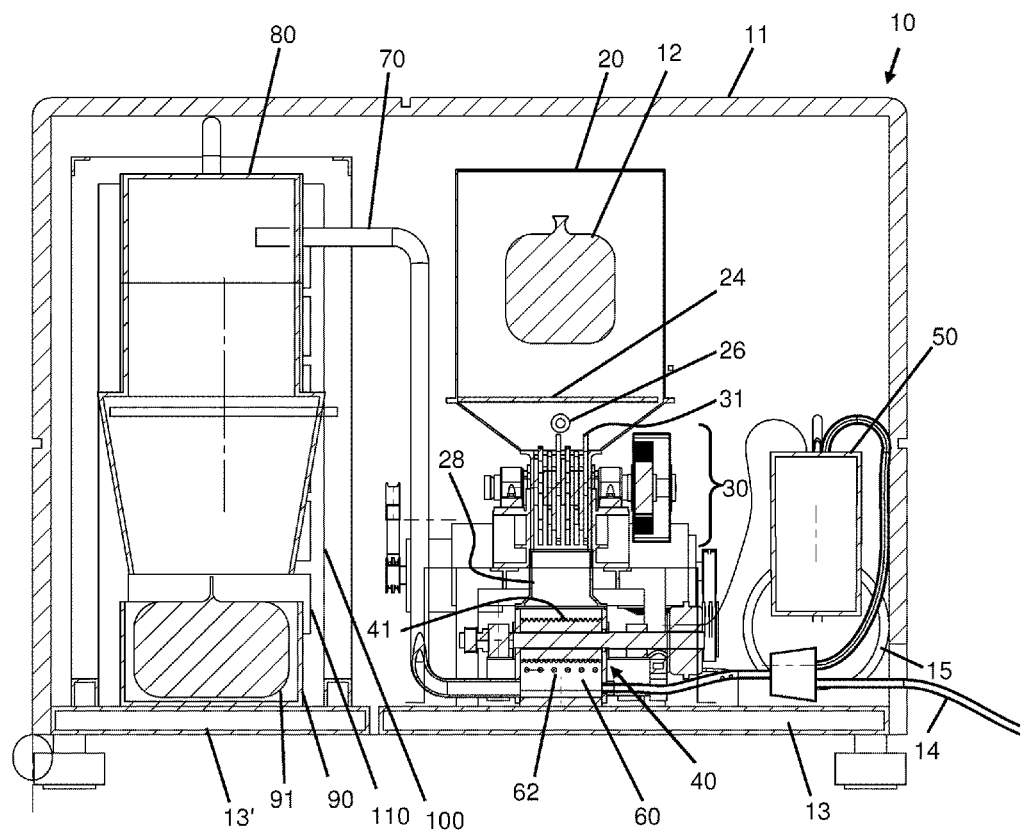
FIGS. 4 and 4A show cross-sections taken from the embodiment of FIG. 3.
Figure 4A:
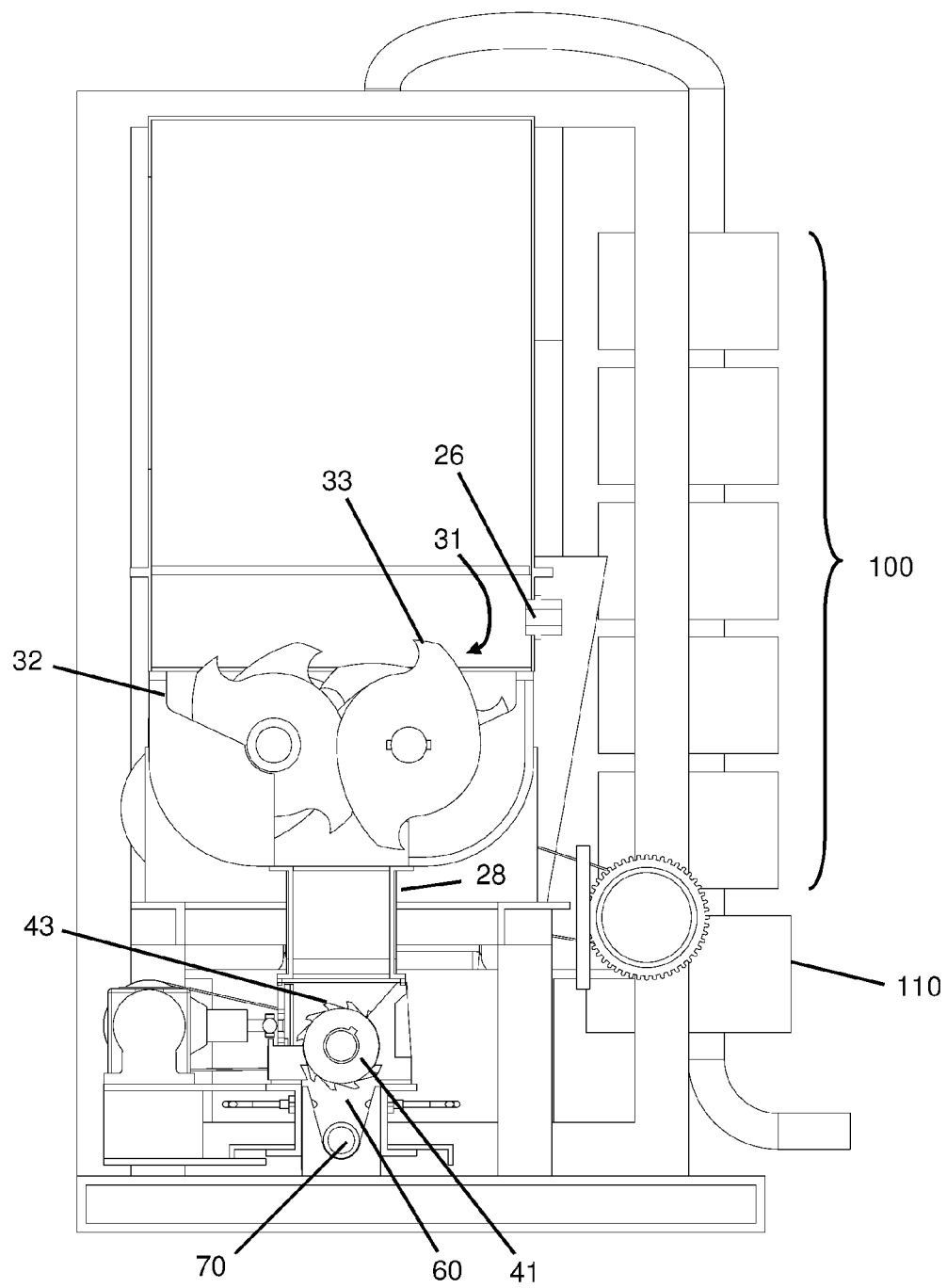

FIG. 3 illustrates an exemplary embodiment of a waste processing system 10 (with outer casing 11 removed for clarity), and FIGS. 4-4A show the indicated cross-sections. The system is enclosed in outer casing 11 for, e.g., isolating the ambient environment from noise, odors, and moving parts inside. Constituent parts of the system may be securely mounted to one or more base plates 13, 13' for stability. Loading chamber 20 includes outer door 22 and inner door 24. Outer casing 11 may have door sufficiently in register with outer 22 to permit placement of waste 12 (shown suspended in mid-air) in the loading chamber. The outer door transitions between an open state that permits a user to place waste in the loading chamber and a closed state that prevents access to the system interior in operation. The outer door may form an airtight seal in the closed state to help seal waste within the system. The inner door transitions between a closed state that provides a surface in the loading chamber on which to place waste and an open state that permits the waste to leave the loading chamber for processing within the system. In some embodiments, the inner door swings up from the closed state to an "open" state in which it provides an airtight seal behind the outer door. The two doors may be connected with one another to provide synchronized movement; i.e., to force the inner door to be in the closed state whenever the outer door is in the open state. The doors may be mechanically and/or electronically interlocked so that only one of them may be in its open state at a given time. In some embodiments, a single door may serve as both inner door and outer door by swinging between a loading state, in which the door adopts the closed state of the inner door, and a sealed state, in which the door adopts the closed state of the outer door.

The loading chamber may also include air inlet 26 and/or detergent inlet (not shown). Air may be admitted into the loading chamber through the air inlet to help the circulation system maintain air flow through the system. Air discharged by the circulation system to generate vacuum may be directed into the loading chamber through the air inlet to maintain a closed circulation, or ambient air may be drawn into the loading chamber through the air inlet. Alternatively, the air inlet may be positioned at the cutting system, described below. If the air inlet is configured to draw in ambient air, it is typically a one-way valve (such as a flap valve) that allows only admittance of air into the system, not exhaust of air to the environment. The air inlet may also be under control of a system controller to permit air flow only when the machine is sealed and operating.

Cutting system 29 may include a first-stage cutting system 30 and a second-stage cutting system 40. The first-stage cutting system receives waste from the loading chamber and includes cutters sized, shaped, and positioned to cut waste into strips. The second-stage cutting system receives waste from the first-stage cutting system and includes cutters sized, shaped, and positioned to cut waste strips into pieces having cross sections no larger than one square inch.

FIGS. 5-11 show an embodiment of a cutting system and component parts in more detail.

Figure 5:
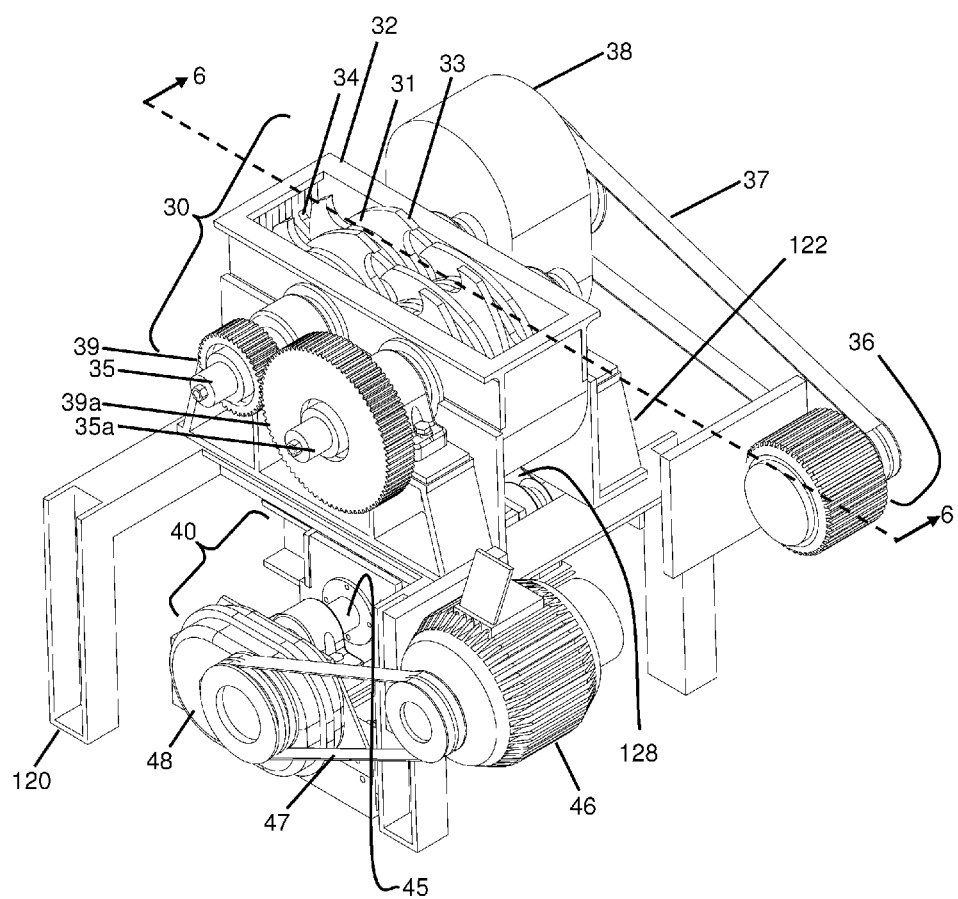
FIG. 5 shows detail of an exemplary embodiment of a cutting system.
Figure 6:
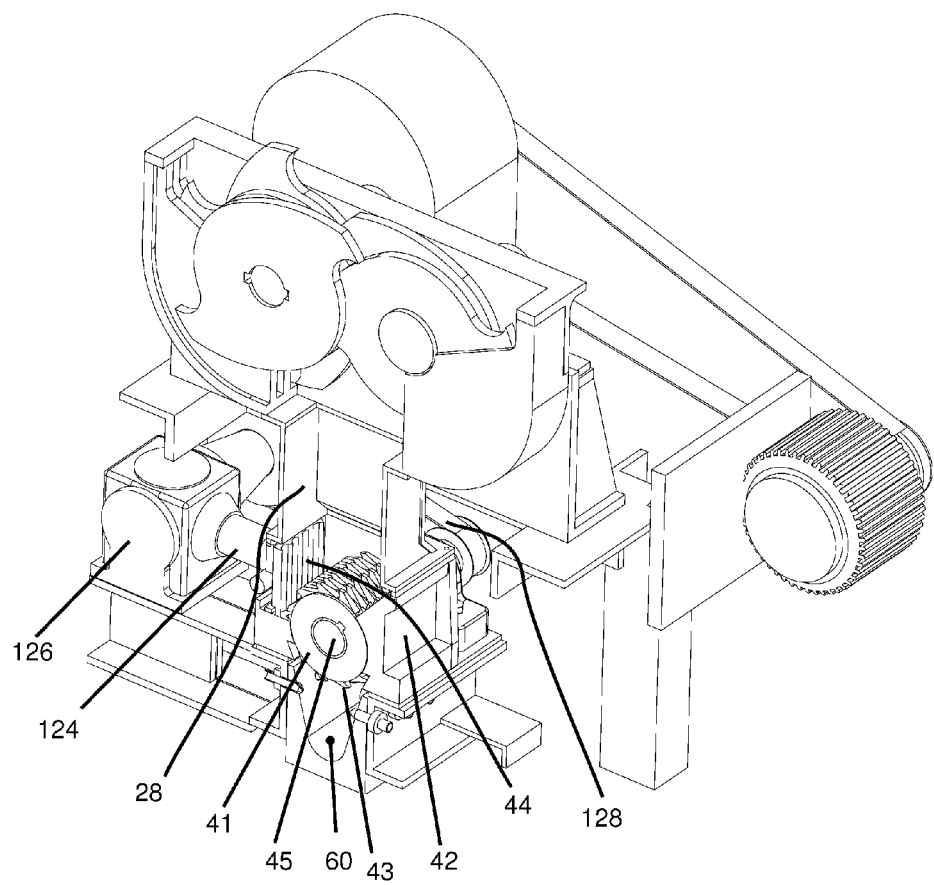
FIG. 6 shows a cross-section taken from the embodiment of FIG. 5.
Figure 7:
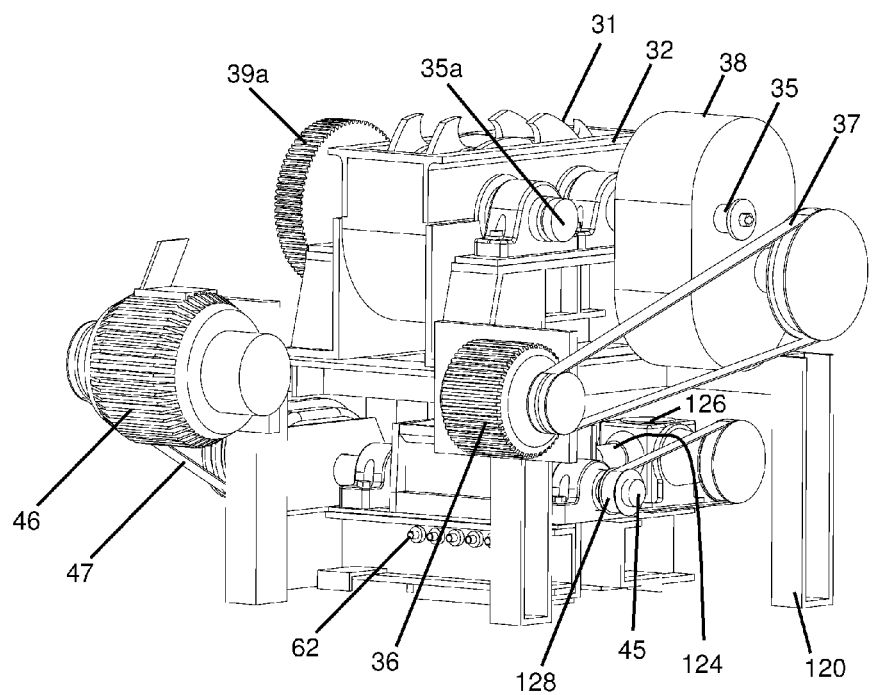
FIG. 7 shows additional detail of the embodiment of FIG. 5.

As shown in FIGS. 5-7, first-stage cutting system 30 may include multiple rotary cutters 31 in a fixed cutter 32. The rotary cutters have cutting tip(s) 33 and are grouped in two sets, each set turned by respective drive shaft 35, 35a. The two sets of cutters overlap, and the individual rotary cutters interleave with one another; in this way, the two sets of rotary cutters cut against one another. Individual rotary cutters also interleave with multiple fins 34 on the fixed cutter. The rotary and fixed cutters are typically packed sufficiently closely together that they intercept and cut essentially all solid non-particulate waste presented to them. As the waste falls between and is pulled by the cutters, the sharpened edges of the cutting tips slice the waste into strips and shear the strips sideways, with little or no crushing.

Thus the size of the first-stage cutting tips, and the length 135 (FIG. 10) between the tips determine the size of the waste strips. In one exemplary embodiment, the cutters are about 0.5 inch wide, the outer edge of the cutting tips are about 1 inch long and described by a circle 11 inches in diameter, so that they are separated by an arc length of about 16 inches; thus, strips of waste up to those dimensions would emerge from the first-stage cutter. The size and shape of the cutters can be modified to suit a particular purpose. To help ensure precise shaping and sharpened edges, the contours of the cutters, especially the rotary cutters, may be flame- or laser-cut from the leading edge of each tip to the trailing edge of the other tip (distance 135 in FIG. 10).

The cutters should be made from materials hard enough to withstand the forces imposed on them during the cutting process. In a typical application of processing medical waste that contains metal, plastic, and other materials, the cutters may have the dimensions given above (outer cutting edges defined by 11-inch circle, 0.5 inch thickness) and be made from tool steel, such as oil hardening steel. One possibility is AISI O1 oil-hardening tool steel. The tool steel may be hardened (by a variety of known techniques, not just oil hardening) to a preferred hardness, such as hardness 58-60 on the Rockwell C scale (HRC 58-60). The fins of the first-stage fixed cutter may also be made from low carbon steel.

The drive shafts are driven by one or more motors. In the depicted embodiment, motor 36 drives belt 37 to turn an axle in first-stage gearbox 38 (such as a speed reducer), which provides rotation for drive shaft 35. The motor and subsequent linkages connecting it to the axle should generate sufficient torque to allow the cutters to carry out the cutting process called for. In some embodiments, such as processing of metal and plastic medical waste, torque developed by the axle may be in the range of 500 foot-pounds to 2,000 foot-pounds, 750 foot-pounds to 1,500 foot-pounds, 900 to 1,200 foot-pounds, 950 to 1,050 foot-pounds, and/or about 1,000 foot-pounds. In some embodiments, force exerted by the cutter tips on the material being processed may be in the range of 1,000 pounds to 4,000 pounds, 1,500 pounds to 3,000 pounds, 1,900 pounds to 2,400 pounds, 2,000 pounds to 2,300 pounds, and/or about 2,200 pounds. In the case of cutters having outer cutting edges defined by an 11-inch circle (0.458 feet from center of rotation to tip), a motor-linkage arrangement generating about 1,000 foot-pounds of torque would present about 2,200 pounds of force at the tips. In one embodiment, a 5 HP motor operating at 1,750 µm (such as a Reliance P18G4903 or Baldor M3665T) produces about 15 foot-pounds of torque, which when coupled by a belt and pulleys with a 2.75 diameter ratio to a 25× speed reducer (such as a Dodge TXT325-BT) will produce about 1,000 foot-pounds of torque at an axle rotating at about 25 rpm and driven by the reducer. An 11-inch cutter rotating on the axle will deliver about 2,200 pounds of force at its tips.

Drive shafts 35 and 35a are coupled by intermeshing gears 39 and 39a, thereby providing rotation for drive shaft 35a. As shown, the gears may be of different sizes (or otherwise differing), so as to have a gear ratio of other than 1:1, thereby causing the two drive shafts to rotate at speeds different from one another (which may improve cutting efficiency by constantly confronting waste with different cutter profiles). Alternatively, the gears may be sized and shaped to maintain the same speed of the two drive shafts. In some embodiments, the two shafts may be driven by two separate motors, at identical or different speeds.

The fixed cutter 32 may be affixed to, or integrally formed with, one or more brackets 122. The bracket(s) may be in turn attached to an additional support 120 that is affixed to a base plate. The bracket(s) and support provide stability and also vertical positioning of the first-stage cutting system relative to other system components.

In normal cutting operation, the rotary cutting blades rotate inwardly, i.e., so that the cutting tips rotate toward one another on the side of the first-stage cutting system to which waste is initially presented (the top side in the embodiment shown). The rotary blades may be capable of reverse motion for various purposes, such as clearing jams.

FIG. 5 also shows external features of second stage cutter 40, including motor 46 that drives second-stage drive shaft 45 by way of belt 47 and second-stage gearbox 48. The second-stage motor may have similar properties as the first-stage motor, discussed above.

FIG. 6 shows the cross-section indicated in FIG. 5 to illustrate further details of the depicted embodiment. Transition zone or chute 28 is positioned between the first- and second-stage cutting systems and channels waste material from the first-stage cutting system to the second-stage cutting system. The chute also provides a space for temporarily holding waste material between the cutting systems. The second-stage cutting system includes second-stage rotary cutter 41 with multiple cutting tips 43, and second-stage fixed cutter 42.

The second-stage cutting system may also include comb 44 that agitates waste as it is presented to the second-stage cutters. The comb shuttles oblique to the motion of the rotary cutter (for example, side-to-side along the rotary cutter's axis of rotation) and may be driven by rotational energy supplied by second-stage drive shaft 45 through belt 128, gearbox 126, and axle 124, although other power schemes are possible, such as a dedicated motor. The comb may have a variety of shapes; the illustrated embodiment has multiple sharp ridges and curved grooves between the ridges; the ridges may be blunt, and the grooves may have straight sides, somewhat like the second-stage fixed cutter 41. The comb may be made, for example, using steel, such as low carbon steel, optionally with a black oxide finish.

Trough 60 is positioned below the second-stage cutting system to receive the completely cut waste.

FIG. 7 shows the embodiment of FIG. 5 from a different perspective to help illustrate various features.

Figure 8:
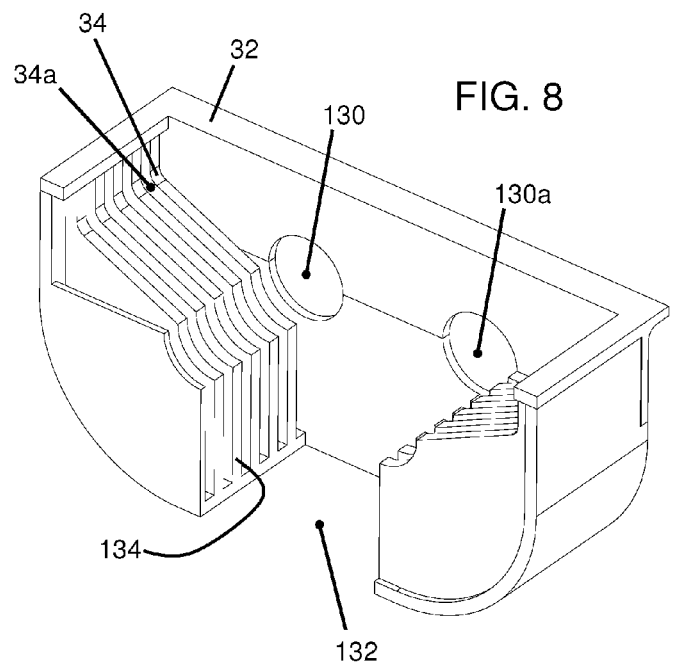
FIGS. 8-10 show detail of portions of an exemplary embodiment of a first-stage cutting system.

FIG. 8 shows detail of the first-stage fixed cutter 32. It defines through-holes 130, 130a for passage of the first-stage drive shafts. Multiple fins 34 extend inwardly from the sides of the fixed cutter and are separated from one another by spaces 34a. The bottom of the fixed cutter defines a gap 132 to allow shredded waste to fall out of the first-stage cutting system; flush ends 134 of the fins may help in part to define the gap.

Figure 9:
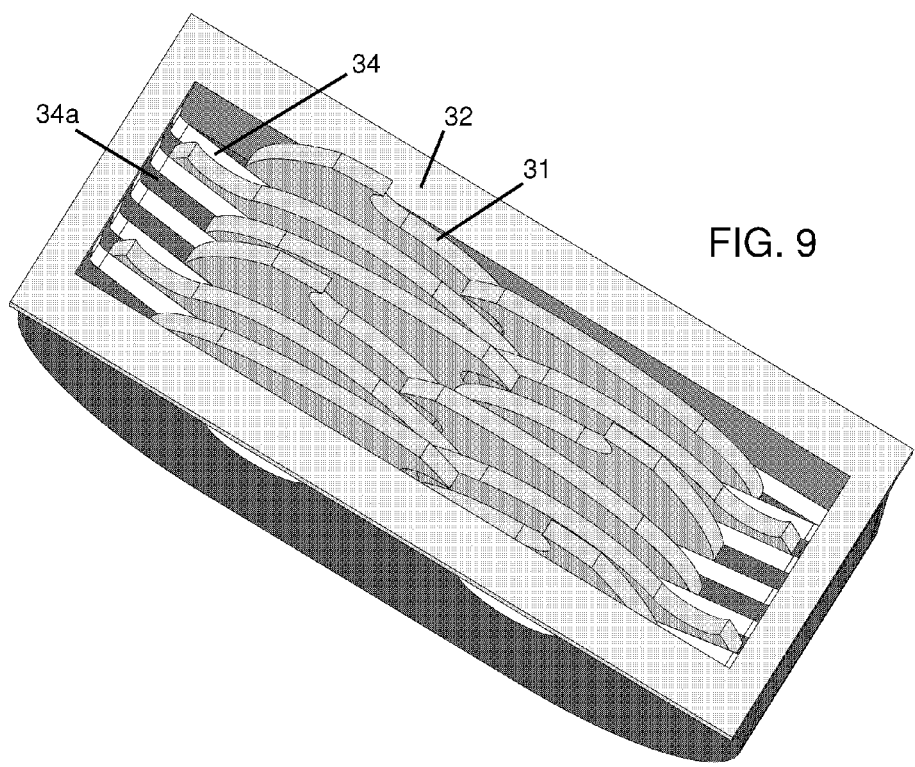

FIG. 9 shows another view of the first-stage fixed cutter 32, now with the rotary cutters 31 in position. The rotary cutters fit into respective spaces 34a, and the two sets of rotary cutters interleave with one another. Fins 34 on the left side of the fixed cutter are staggered with respect to those on the right side.

Figure 10:
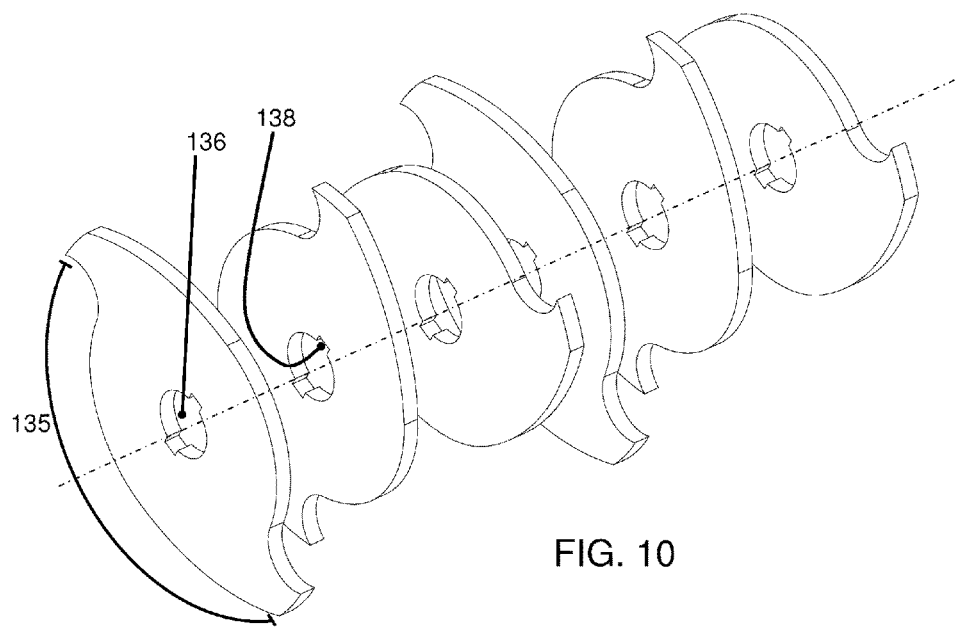

FIG. 10 shows an exploded view of one set of first-stage rotary cutters (i.e., from the left or right side of the fixed cutter). Each cutter defines a central hole 136 through which the drive shaft passes. Each cutter further defines or includes a feature, such as the illustrated keyway 138, that corresponds to a complementary feature on the drive shaft (e.g., a key or rail, not shown in the drawings or represented in the appended computer program listing) to prevent rotation of the cutters relative to the drive shaft. In the depicted embodiment, the features on the cutters are oriented at positions different from one another such that the various cutters are rotationally fixed to the draft shaft with their cutting tips 33 at different angles; such angle variation among cutters may increase cutting efficiency. The slight hook shape to the cutting tips can help pull waste into the cutting system, in synergy with the vacuum applied by the circulation system. The hooks on one set of rotary cutters rotate toward the other set, and vice-versa.

Figure 11:
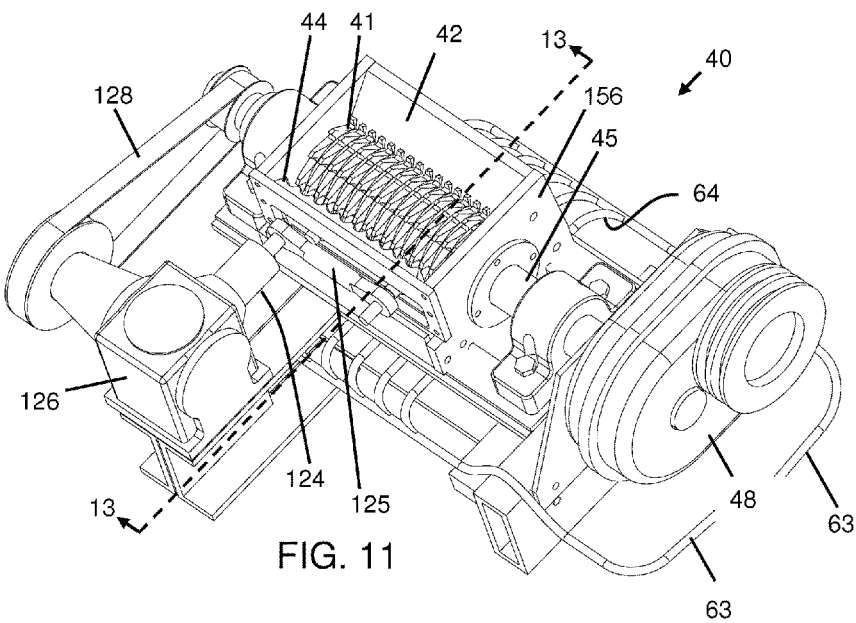
FIGS. 11-13 show detail of portions of an exemplary embodiment of a second-stage cutting system.
Figure 12:
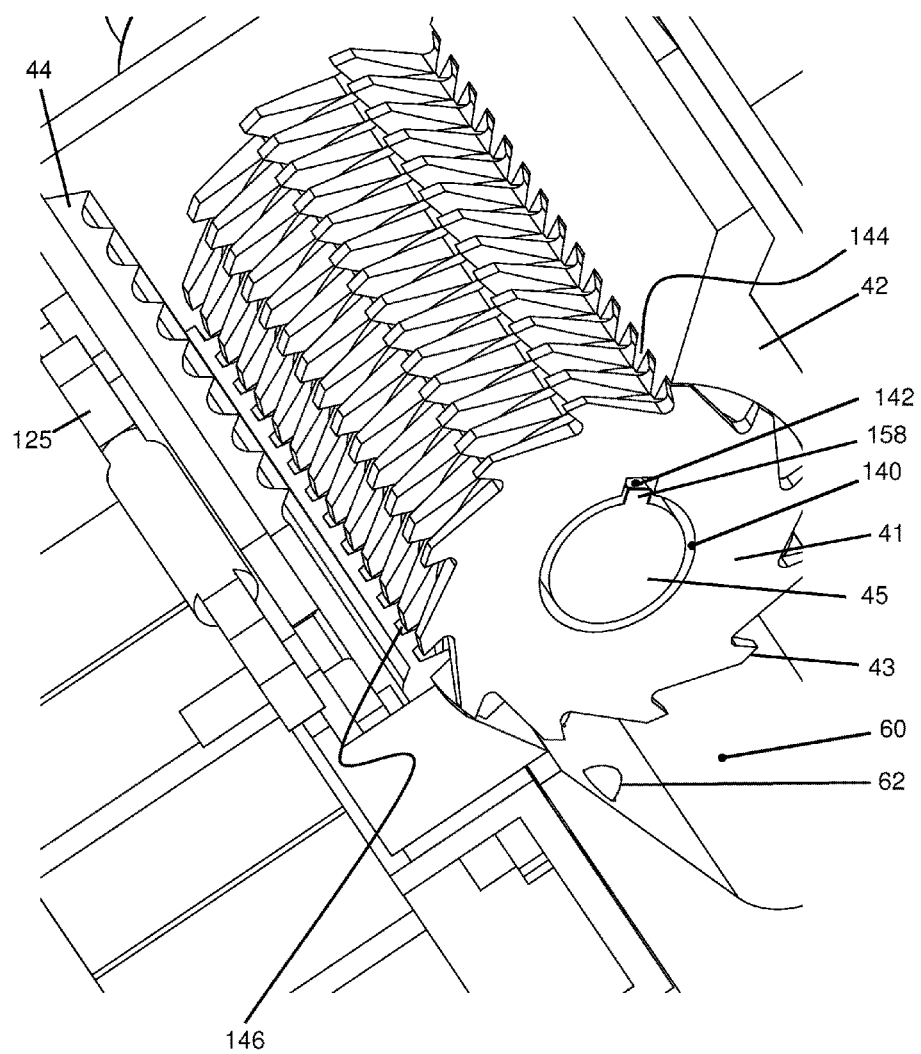
Figure 13:
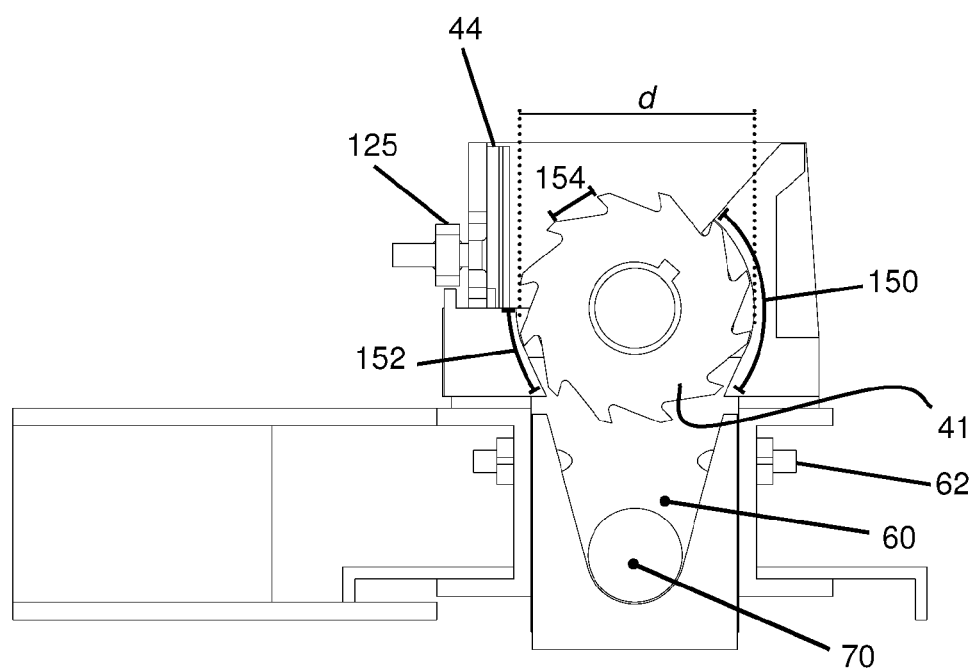

FIGS. 11-13 provide greater detail of the second-stage cutting system 40.

As shown in FIG. 11 and noted previously, drive shaft 45 is powered by motor 46 (not shown) through gearbox 48 and turns second-stage cutter 41. Second-stage fixed cutter 42 defines multiple fins 144 separated by spaces 146; the rotary cutters turn in the spaces to shear the shredded waste from the first-stage cutting system. Comb 44 shuttles side-to-side to help agitate and position waste strips for shearing; the comb is powered either through a linkage (i.e., axle 124, gearbox 126, and belt 128 driven by drive shaft 45) to motor 46 or by another motor. Linear movement of the comb may be obtained by using a screw drive, rack-and-pinion system, linear friction actuator, or other linkage for converting rotational motion to linear motion. Disinfectant supply lines 63 conduct disinfectant to trough 60 (not shown); individual feeder lines 64 may be provided to direct disinfectant into disinfectant inlets 62 (not shown).

FIG. 12 provides a close-up view of a portion of the second-stage cutting system, with side plate 156 removed for clarity. Second-stage rotary cutter 41 has multiple cutting tips 43 protruding from its surface, which are sized, shaped, and positioned on the cutter to be in register with spaces 146 on the second-stage fixed cutter 42. Cutter 41 has a tubular shape defining a bore 140 through which drive shaft 45 passes. The cutter further defines or includes a feature, such as the illustrated keyway 142, that corresponds to a complementary feature on the drive shaft (e.g., a key or rail 158, not represented in the appended computer program listing) to prevent rotation of the cutters relative to the drive shaft, largely as described earlier for the first-stage cutters.

Cutting tips 43 are in register with corresponding spaces 146 and are complementarily shaped to the grooves. In the depicted embodiment, the tips are chamfered (i.e., they taper toward their free ends), and the grooves are chamfered at the same angle. As a result, the clearance between the tips and the grooves can be made quite small, such as in the range of 0.00005 inch to 0.01 inch and typically 0.001 (one-thousandth) inch. Such small clearance helps ensure that waste entering the second stage cutting system has nowhere to go but between the cutters. As the waste is forced between the cutters, the sharpened edges of the cutting tips slice the waste longways and shear it sideways, with little or no crushing.

Thus the size of the second-stage cutting tips, and the length 154 (FIG. 13) between the tips determine the final maximum size of the waste pieces. In the depicted embodiment, there are 12 teeth around the circumference of the cutter, which has a diameter d of about 5 inches; the tips have a separation length 154 of about $\frac{1}{5}$ d (1 inch) and a width at the free end of about $\frac{1}{20}$ d (0.25 inch). The fixed cutter has similar dimensions to the tips, within small tolerances; as a result, the dimensions given above are the theoretically maximum dimensions of waste pieces emerging from the cutting system. In practice, waste strips and pieces tumble about as they pass through the cutting system and are cut multiple times, so that the pieces have final dimensions no larger than smallest cutting dimension (0.25 inch in the example given here). These relative and absolute dimensions are provided for illustrative purposes only and are not essential; relative dimensions between diameter, separation, and width may vary.

Cutter 41 is shown as a single piece, but it could be replaced by a set of disks, each with one or more ranks of teeth about their circumferences.

The rotary and fixed cutters of the second stage cutting system may be made of similar materials as those, such as tool steel, in particular, AISI O1 oil hardening tool steel hardened to HRC 58-60.

FIG. 13 shows the cut section indicated in FIG. 11. Fixed cutter 42 and rotary cutter 41 interact in arcuate side zones 150, 152; space above the rotary cutter is free in order to provide a clear path for waste strips emerging from the first-stage cutting system and transition zone; space below the rotary cutter is free to provide a clear path for waste pieces to fall into trough 60.

One or more agitators can be positioned between the loading chamber, the first-stage cutting system, and the second-stage cutting system to jostle waste as it passes through and dislodge jams. A metering device may also be positioned between the stages to help feed waste into the second-stage cutting system at a regulated rate.

Waste exits the cutting system in the form of small pieces, typically having cross-sections no larger than one square inch (such as one inch by one inch square), 0.25 $in^2$ (such as half-inch by half-inch square), and/or 0.0625 $in^2$ (such as quarter inch by quarter inch square). The cutters of the cutting system are sized, shaped, and positioned in order to cut down waste to the desired size. The cutter arrangement, therefore, can help ensure that no piece of waste has any dimension larger than a set limit, such as one inch, 0.5 inch, or 0.25 inch.

Waste leaves the cutting system and passes into a trough 60, where disinfectant from disinfectant source 50 is sprayed through disinfectant inlets 62, such as jets, onto the waste. As noted previously, agitation of waste by the circulation system 110 helps expose all facets of the waste pieces to the disinfectant. The circulation system will typically apply sufficient vacuum to suck waste through the system at least 75 miles per hour. For example, in the illustrated embodiment, in which wetting tunnel 70 extends vertically several feet, such pressure overcomes gravity to ensure that material passes through the wetting tunnel without falling to the bottom.

The disinfectant will typically be a liquid, although it may also be a gas or a powder. The disinfectant may be an alkaline solution, such as an aqueous alkaline solution. The solution may have a pH of at least 12. In one embodiment, the disinfectant is a pH 12 or greater aqueous solution of calcium oxide (CaO); a 10% solution ("milk of lime") is typically used. A principal source of CaO is kiln dust. Because CaO degrades rapidly on exposure to air and moisture, it may be stored in dry powder form and put in solution (such as mixing with water supplied from line 14) shortly before being sprayed into the waste processing system.

Sprayed waste pieces are sucked from the trough into wetting tunnel 70, where agitation continues. Additional jet(s) may be provided in the wetting tunnel to aid the wetting and disinfection process. The length of the wetting tunnel is not critical; disinfection occurs substantially on contact. In some embodiments, therefore, the wetting tunnel may be omitted, and waste passes from the trough to the separator.

Separator 80, such as a cyclone separator, may be used to divide the disinfected waste by size into pieces large enough to settle quickly into receiving bin 90 (such as into refuse bag 91) and particulate matter that will not settle so readily. The large pieces, constituting the bulk waste, typically fall by gravity out of the separator in the receiving bin, while particulate matter remains suspended in the air stream generated by the circulation system and directed into filter system 100. If the input waste includes liquid, the liquid can similarly fall out of the separator into a refuse bag.

The filter system 100 can include a number of components, including a bag filter, an odor filter, a HEPA filter, and/or a noise-reduction muffler. The bag filter can be used to trap the vast majority of the particulate waste; little waste, except the finest particulate matter, may escape the bag filter. The odor filter may be used to capture gases in the air to reduce bad odors. The HEPA filter may be a very fine filter that will capture particulate matter, if any, that evaded the bag filter. The main vacuum source for the circulation system may be positioned among the filter system components, for example, downstream of the bag filter and upstream of other filter components.

The waste processing system may include a controller, such as a computer, that provides a command console for an operator. The controller may also record information about operational parameters, such as run times, waste throughput, operator identification, and status of system components, such as empty/full status of the loading chamber, cutting system, disinfectant source, receiving bin, and filter system. The controller can also receive sensory data from within the system, such as weight scale(s) in the loading chamber and receiving bin to monitor accumulation of waste, and torque and/or motion sensors in the cutting system to detect jams. The controller can command operation of the cutting system and operate it in a variety of modes depending on type of waste input or need to remove a jam.

In one exemplary embodiment, a waste processing method includes (a) placing infected waste in the loading chamber; (b) closing the loading chamber door, thereby sealing the infected waste inside the waste processing system; (c) opening the trap door, thereby allowing the infected waste to leave the loading chamber and contact the first-stage cutting system; (d) actuating the circulation system to apply sufficient vacuum through the filter system, the wetting tunnel, the trough, the second-stage cutting system, the first-stage cutting system, and the loading chamber to suck waste therethrough; (e) operating the cutting system on infected waste to cut it into pieces having cross sections no larger than one square inch, the pieces advancing to the trough; (f) spraying disinfectant into the trough as the infected waste pieces pass therethrough, thereby coating the waste pieces with disinfectant and disinfecting them; (g) sucking the waste pieces through the trough, through the wetting tunnel, and into the separator; (h) separating material received by the separator into disinfected particulate waste matter and disinfected bulk waste matter; (i) advancing bulk waste matter into the receiving bin; and (j) trapping particulate waste matter in the filter system.

The various components of the waste processing system described herein may be used individually for other purposes. In particular, the disclosed cutting system may be used for other applications requiring size reduction of input material. For example, the cutting system may be used to reduce the size of waste that does not require pathogen reduction or has already been treated for pathogen reduction. The cutting system may be used for shredding and shearing a wide variety of materials, such as metal, plastic, paper, glass, wood, euthanized animals, animal waste- and by-products, organic matter, etc. Exemplary uses include preparing materials for recycling, for space-efficient disposal, for use as filler, and for obliterating identifying characteristics.

EXAMPLE

The waste processing system embodiment illustrated in the drawings is also represented in the Virtual Reality Modeling Language (VRML version 1.0) computer program listing accompanying this specification ("example-wrl.txt" in the computer program listing appendix). While the dimensions of objects in the representation reflect those of mechanical drawings and a prototype prepared to the inventor's specifications, they (and indeed all relative and absolute dimensions disclosed herein) are provided for illustrative purposes only and are not intended to be limiting unless expressly claimed.

I claim:

1. A cutting method comprising:
   providing a cutting system, the cutting system comprising:
      a first-stage cutting system comprising:
         a fixed cutter comprising:
            a first set of fins extending inwardly from a first wall of the fixed cutter, the fins separated by gaps; and
            a second set of fins extending inwardly from a second wall of the fixed cutter, the fins separated by gaps;
            wherein the first set of fins and the second set of fins are staggered with respect to one another so that the fins of the first set are aligned with the gaps separating the fins of the second set; and
         a first set of rotary cutters having sharpened cutting surfaces and being
            mounted on a first axle and
            positioned to rotate through the gaps between the first set of fins; and
         a second set of rotary cutters having sharpened cutting surfaces and being
            mounted on a second axle, separated from and parallel to the first axle, the second set of rotary cutters
            positioned to interleave and counter-rotate with the first set of rotary cutters and to rotate through the gaps between the second set of fins;
      a second-stage cutting system comprising:
         a fixed cutter comprising fins separated by gaps;
         a rotary cutter mounted on a third axle and comprising sharpened teeth that are positioned in register with the gaps of the second-stage fixed cutter so that the teeth rotate through those gaps;
         a chute positioned to channel material emerging from the first-stage cutting system into the second-stage cutting system;
         a comb positioned adjacent the rotary cutter and fixed cutter of the second-stage cutting system, the comb comprising a plurality of ridges and grooves facing the rotary cutter;
         a transmission system coupling the third axle to the comb; and
         a motor driving the third axle and the comb;
      introducing a material to be cut into the first-stage cutting system of the cutting system;
      counter-rotating the first and second axles so that the first-stage rotary cutters shred the material;
      advancing the material, or allowing the material to advance, through the chute and into the second-stage cutting system; and
      rotating the third axle so that the second-stage rotary cutter shears the shredded material against the second-stage fixed cutter, and the comb moves with motion oblique to that of the second-stage rotary cutter.

2. The method of claim 1, wherein each first-stage rotary cutter defines a keyway complementary to a key on the respective axle.

3. The method of claim 2, wherein keyways of different first-stage rotary cutters are oriented at different angles relative to each cutter's sharpened cutting surfaces.

4. The method of claim 1, wherein the system further comprises a first motor driving the first axle.

5. The method of claim 4, wherein the system further comprises a first gear mounted to the first axle and meshing with a second gear mounted to the second axle, so that the first motor drives both the first and second axles.

6. The method of claim 5, wherein the first and second gears have a gear ratio other than 1:1, so that the first and second axles rotate at different speeds when driven by the first motor, and material being shredded by the first-stage cutting system is thereby constantly confronted with different cutting profiles.

7. The method of claim 4, wherein the motor is coupled to the axle by one or more linkages, and the motor and linkage(s) are selected to develop a torque at the first axle in the range of 500 foot-pounds to 2,000 foot-pounds.

8. The method of claim 1, wherein the comb is constrained to motion parallel to a long axis of the third axle.

9. The method of claim 1, wherein the transmission system comprises a linkage for converting rotational motion to linear motion.

10. The method of claim 1, wherein the system further comprises a metering device positioned between the first- and second-stage cutting systems to regulate a material flow rate between the stages.

11. The method of claim 1, wherein the system further comprises a controller coupled to the motor and programmed to control the motor's mode of operation.

12. The method of claim 11, wherein the system further comprises at least one sensor (a) positioned in the cutting system to measure torque or motion in the cutting system and (b) coupled to the controller to transmit a signal to the controller indicative of the measure, and the method further comprises measuring torque or motion in the cutting system; and transmitting a signal indicative of the torque or motion to the controller.

13. The method of claim 12, wherein the controller is programmed to operate the motor in reverse when the signal is indicative of a jam in the cutting system, and the method further comprises operating the motor in reverse when the signal is indicative of a jam in the cutting system.

14. The method of claim 1, wherein air inside the cutting system is isolated from the system's surrounding environment, and wherein the system further comprises a vacuum source positioned to apply vacuum through the system, and the method further comprises applying vacuum to the cutting system to pull the material through the system.

15. The method of claim 1, wherein the first set of rotary cutters are mounted on the first axle such that sharpened cutting surfaces of different ones of the first set of rotary cutters are oriented at different angles relative to one another; and the second set of rotary cutters are mounted on the second axle such that sharpened cutting surfaces of different ones of the second set of rotary cutters are oriented at different angles relative to one another.

16. The method of claim 1, wherein the cutting surfaces of the first and second sets of rotary cutters comprise sharpened hooks, and the first and second sets of rotary cutters are arranged so that the hooks of the first set of rotary cutters rotate toward the second set of rotary cutters and the hooks of the second set of rotary cutters rotate toward the first set of rotary cutters.

17. The method of claim 1, wherein the fixed cutter and the first and second sets of rotary cutters are packed sufficiently closely together that they intercept and cut essentially all solid nonparticulate material presented to them.

18. The method of claim 1, wherein a bottom of the fixed cutter and flush ends of the fixed cutter fins define a bottom gap of the fixed cutter through which shredded material falls out of the first-stage cutting system.

19. The method of claim 1, wherein as the material falls between the rotary cutters it is pulled into the first-stage cutting system by the hooks of the rotary cutters, and the sharpened cutting surfaces of the rotary cutters slice the waste into strips and shear the strips sideways, with little or no crushing.

20. The method of claim 1, wherein the comb comprises multiple sharp vertically-oriented ridges and curved grooves between the ridges.

* * * * *